United States Patent [19]

Kamata et al.

[11] Patent Number: 4,502,989

[45] Date of Patent: Mar. 5, 1985

[54] ALDOSTERONE-ANTAGONISTIC STEROIDS

[75] Inventors: Susumu Kamata, Hyogo; Takeaki Matsui; Nobuhiro Haga, both of Osaka, all of Japan

[73] Assignee: Shionogi & Co., Ltd., Osaka, Japan

[21] Appl. No.: 568,878

[22] Filed: Jan. 5, 1984

[30] Foreign Application Priority Data

Jan. 31, 1983 [JP] Japan .................................. 58-14980

[51] Int. Cl.³ ............................................... C07J 1/00
[52] U.S. Cl. .............................. 260/239.57; 260/397.1
[58] Field of Search ................................... 260/239.57

[56] References Cited

U.S. PATENT DOCUMENTS 4,129,564 12/1978 Wiechert et al. .............. 260/239.57

Primary Examiner—Elbert L. Roberts
Attorney, Agent, or Firm—Wenderoth, Lind & Ponack

[57] ABSTRACT

Novel spironolactone derivatives characterized by the $C_{11}$–$C_{12}$ double bond which have a potent aldosterone-antagonistic activity without causing potassium loss, used alone in diagnosis and improvement of condition of primary aldosteronism, or together with other drugs in treatment of essential or renal hypertension as well as cardiac or renal edema; prepared from 3,17-bis(ethylene-dioxy)-5,11-androstadiene.

15 Claims, No Drawings

ALDOSTERONE-ANTAGONISTIC STEROIDS

BACKGROUND OF THE INVENTION

1. Field of the Invention

The present invention relates to steroid derivatives having aldosterone-antagonistic activity more potent than that of spironolactone.

2. Description of the Prior Art

The aldosterone antagonists have widely been used alone in diagnosis and improvement of condition of primary aldosteronism, or together with other drugs in treatment of essential or renal hypertension as well as cardiac or renal edema since they antagonize aldosterone in the distalis urinary tubule to inhibit resorption of sodium and excretion of potassium and exhibit diuretic effect without causing potassium loss.

Spironolactone [The Merck Index 10th Edition 8610] is a well known aldosterone antagonist. As the analogous compounds of spironolactone are exemplified potassium canrenoate [Clin. Pharm. Ther. 21, 602 (1977)], potassium mexrenoate [J. Pharmacol. Exp. Ther. 209, 144 (1979)], potassium prorenoate [Clin. Pharm. Ther. 18, 391 (1975)], spirorenone [Japanese Unexamined Patent Publication No. 55-162799], and the like. In addition to the above aldosterone antagonists, various steroidal derivatives have been found out as antagonists, among which the compound having a double bond at the $C_{11}$–$C_{12}$ position shown by the following formula is described in French Medicinal Pat. No. 7871.

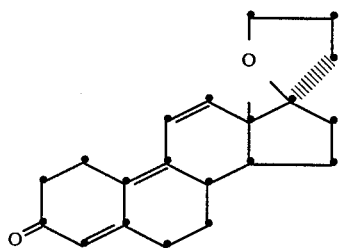

BRIEF SUMMARY OF THE INVENTION

The present invention relates to steroid derivatives having aldosterone-antagonistic activity represented by the following general formula (A):

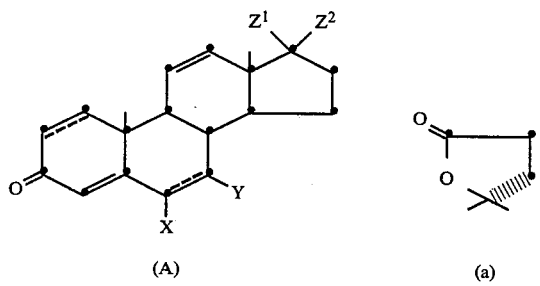

[wherein X is hydrogen, halogen, or hydroxy; Y is hydrogen, lower alkyl, halogen, alkylthio, acylthio, acyloxy, or alkoxycarbonyl; or X and Y taken together form methylene group; $Z^1$ is hydroxy; $Z^2$ is alkali metal salt of carboxyethyl, or $Z^1$ and $Z^2$ taken together with the adjacent carbon atom form lactone ring represented by the above partial formula (a); the broken lines of the positions $C_1$–$C_2$ and $C_6$–$C_7$ indicate the presence or absence of a double bond].

The steroid derivatives of the present invention are novel compounds and characterized by the double bond at the $C_{11}$–$C_{12}$ position of the steroid nucleous structure; they have a potent aldosterone-antagonistic activity and are useful compounds of which the pharmacological efficacy is expected to be applied in a medical field.

The compounds (A) can be prepared from the starting compound 3,17-bis(ethylenedioxy)-5,11-androstadiene [Japanese Unexamined Patent Publication No. 51-26866].

DETAILED DESCRIPTION OF THE INVENTION

The present invention relates to steroid derivatives having aldosterone-antagonistic activity represented by the following general formula (A):

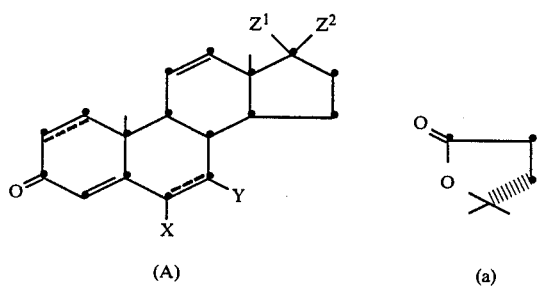

[wherein X is hydrogen, halogen, or hydroxy; Y is hydrogen, lower alkyl, halogen, alkylthio, acylthio, acyloxy, or alkoxycarbonyl; or X and Y taken together form methylene group; $Z^1$ is hydroxy; $Z^2$ is alkali metal salt of carboxyethyl, or $Z^1$ and $Z^2$ taken together with the adjacent carbon atom form lactone ring represented by the above partial formula (a); the broken lines of the positions $C_1$–$C_2$ and $C_6$–$C_7$ indicate the presence or absence of a double bond].

The meanings of the terms used in the above definition are shown below:

the halogen means fluorine, chlorine, bromine, iodine, and the like; the lower alkyl means $C_1$–$C_5$ straight or branched chain alkyl, for example, methyl, ethyl, propyl, isopropyl, butyl, isobutyl, t-butyl, pentyl, isopentyl, and the like; the alkylthio means $C_1$–$C_5$ alkylthio, for example, methylthio, ethylthio, propylthio, isopropylthio, butylthio, isobutylthio, t-butylthio, pentylthio, isopentylthio, neopentylthio, and the like; the acylthio includes benzoylthio and $C_1$–$C_5$ alkanoylthio, for example, formylthio, acetylthio, propionylthio, butyrylthio, isobutyrylthio, valerylthio, isovalerylthio, t-valerylthio, and the like; the acyloxy includes benzoyloxy and $C_1$–$C_5$ alkanoyloxy, for example, formyloxy, acetyloxy, propionyloxy, butyryloxy, isobutyryloxy, valeryloxy, isovaleryloxy, t-valeryloxy, and the like; the alkoxycarbonyl means $C_2$–$C_6$ alkoxycarbonyl, for example, methoxycarbonyl, ethoxycarbonyl, propoxycarbonyl, isopropoxycarbonyl, butoxycarbonyl, isobutoxycarbonyl, t-butoxycarbonyl, pentyloxycarbonyl, isopentyloxycarbonyl, neopentyloxycarbonyl, and the like; the alkali metal salt means sodium salt, potassium salt, and the like.

The compounds of the present invention represented by the above general formula (A) can be prepared from the starting compound (I) 3,17-bis(ethylenedioxy)-5,11- androstadiene [Japanese Unexamined Patent Publication No. 51-26866] according to the reaction sequence described below:
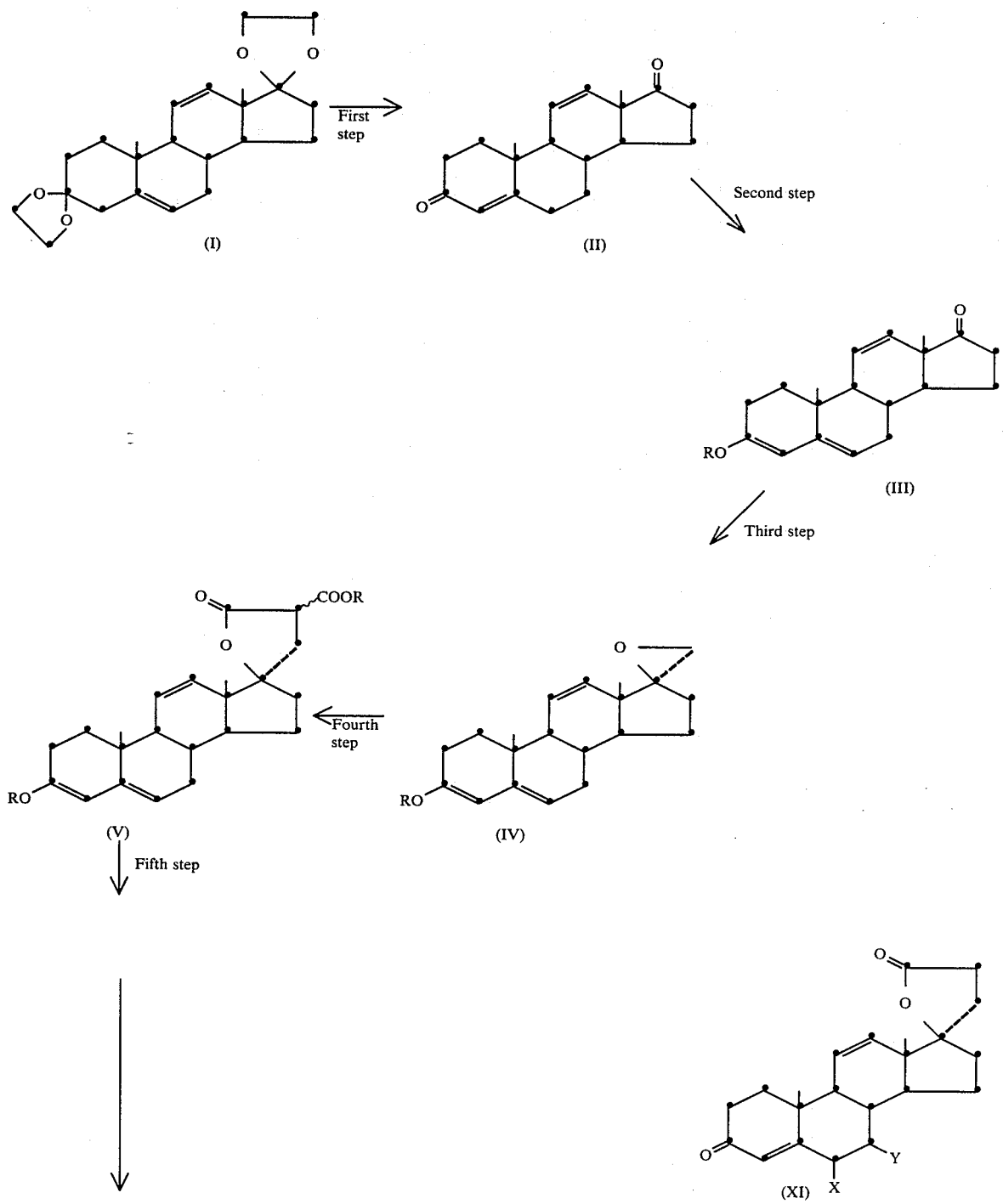

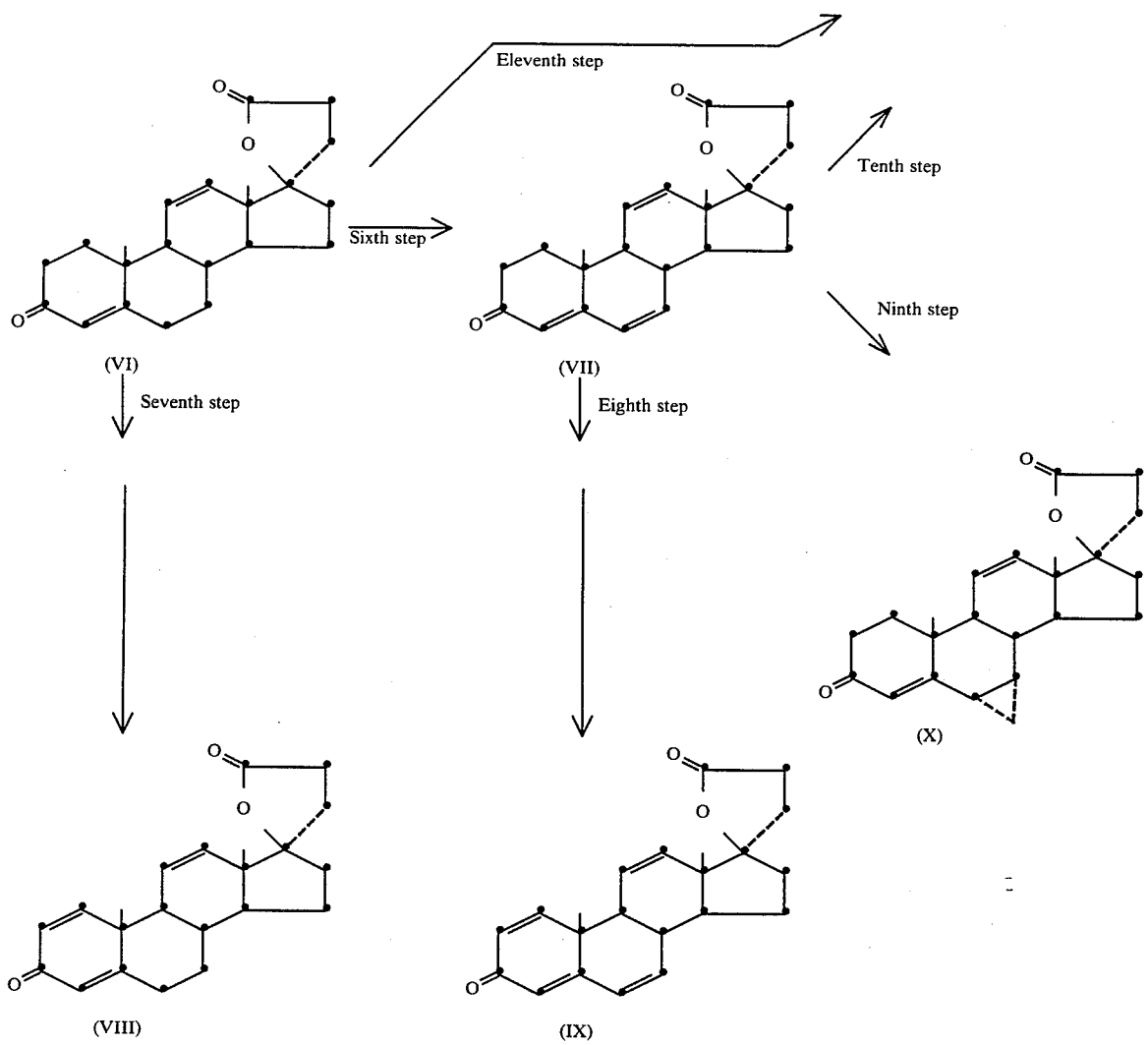

[wherein X is hydrogen, halogen, or hydroxy; Y is hydrogen, lower alkyl, halogen, alkylthio, acylthio, acyloxy, or alkoxycarbonyl; R is methyl, ethyl, benzyl, and the like].

First step

In the first step, the ketals are hydrolyzed to ketones in the presence of an acid catalyst. As the acid catalyst, inorganic acids such as perchloric acid, hydrochloric acid, sulfuric acid, etc., or benzenesulfonic acid, p-toluenesulfonic acid and the like may be used. The solvents which are miscible with water such as methanol, ethanol, tetrahydrofuran, dioxane, acetone, etc. may be used, in the presence of water. The reaction is conducted at room temperature or with heating, and terminates within a period of several minutes to several hours.

Second step

In the second step, the ketone at the 3 position is enolized to the 3-alkoxy compound having the double bonds at the positions $C_3-C_4$ and $C_5-C_6$. In the enolization, alkylating agents, for example, 2,2-dimethoxypropane, methyl orthoformate, and ethyl orthoformate are preferably employed in the presence of acid catalysts such as p-toluenesulfonic acid, sulfuric acid, and the like. As the solvents, aprotic solvents such as ether, tetrahydrofuran, dioxane, glyme, diglyme, benzene, toluene, and the like may be used, and the reaction usually terminates at room temperature within a period of several minutes to several hours.

Third step

In the third step, a highly selective methylene-transfer reagent acts on the carbon atom at the 17 position to form the epoxide. The reaction is carried out with dimethylsulfonium methylide as a methylene-transfer reagent provided from the reaction of trimethylsulfonium iodide with sodium methylsulfinylmethide which is prepared by heating a mixture of sodium hydride and dimethylsulfoxide at 65°–75° C. for several minutes to several hours until evolution of hydrogen gas ceases. As the solvents, a mixture of dimethylsulfoxide and aprotic solvents such as ether, tetrahydrofuran, dioxane, glyme, diglyme, benzene, toluene, and the like may be used, and the reaction is conducted with cooling or at room temperature, and terminates within a period of several hours to several days.

Fourth step

In the fourth step, the compound (IV) is converted into the compound (V) on cleavage of the epoxy ring with a dialkyl malonate in the presence of a base. As the base, sodium methoxide or sodium ethoxide is preferred. As the solvents, alcoholic solvents such as methanol, ethanol, and the like may be used. The reaction is conducted under reflux with heating, and terminates within a period of several hours. The product can be used in the next step without isolation.

Fifth step

In the fifth step, the compound (V) is hydrolyzed with an alkali to remove the alkoxycarbonyl group at the 21 position, and the resulting alkali metal salt of γ-hydroxycarboxylic acid is treated with an acid, or the free γ-hydroxycarboxylic acid is heated under a condition for dehydration to give the γ-lactone. As the alkali, lithium hydroxide, sodium hydroxide, potassium hydroxide, and the like may be used. As the acids, hydrochloric acid, sulfuric acid, p-toluenesulfonic acid, and the like may be used. The reaction giving the γ-lactone compound is carried out under the dehydration condition with heating in a solvent such as xylene, bromobenzene, chlorobenzene, or the like. The reaction terminates within a period of several hours.

Sixth step

In the sixth step, the double bond at the $C_6$–$C_7$ position is formed with dehydrogenating agents under a thermodynamic condition, e.g. in the presence of an acid. As the dehydrogenating agents, quinone-type ones such as tetrachloro-1,4-benzoquinone (chloranil), 2,3-dichloro-5,6-dicyanobenzoquinone (DDQ), and the like may be used. As the acid catalysts, hydrochloric acid, sulfuric acid, acetic acid, benzenesulfonic acid, p-toluenesulfonic acid, and the like may be used. As the solvents, alcoholic solvents such as methanol, ethanol, n-pentanol, sec-pentanol, and t-butanol; ether solvents such as dioxane, ether and tetrahydrofuran; aromatic solvents such as benzene and toluene; and acetic acid, and the like may be used. The reaction is conducted at room temperature or under reflux with heating, and terminates within a period of several hours.

The reaction of 3,5-dienol ether derivatives of the compound (VI) with DDQ etc. also affords the compound (VII).

Seventh step

In the seventh step, the double bond at the $C_1$–$C_2$ position is formed with dehydrogenating agents under a kinetically controlled condition. As the dehydrogenating agents, quinone-type ones suhh as DDQ having high oxidation activity or selenium dioxide can be used. As the solvents, alcoholic solvents, ether solvents, or aromatic solvents may be used; when selenium dioxide is used as dehydrogenating agent, t-butanol is preferably used as solvent. The reaction terminates under reflux with heating within a period of several hours.

Eighth step

In the eighth step, a double bond is formed at the $C_1$–$C_2$ position with dehydrogenating agents such as DDQ, and the reaction may be conducted in the same manner as in the seventh step.

Ninth step

In the ninth step, the methylene group is introduced between the positions $C_6$ and $C_7$ with methylene-transfer reagents. The reaction is conducted in dimethylsulfoxide with dimethylsulfoxonium methilide as methylene-transfer reagent provided from the reaction of trimethylsulfoxonium iodide with sodium hydride in dimethylsulfoxide. The reaction terminates within a period of several hours with cooling or at room temperature.

Tenth step

In the tenth step, the compound (VII) is subjected to addition reaction at the $C_6$–$C_7$ double bond. In order to introduce alkylthio at the 7α position, a mixture of the compound (VII) and alkylthiol is heated under reflux for a period of several minutes to several hours in the presence or absence of a base. As the solvents, aprotic solvents such as ether, tetrahydrofuran, dioxane, glyme, diglyme, benzene, toluene, and the like may be used. In order to introduce acylthio at the 7α position, the compound (VII) is heated under reflux in thiocarboxylic acid for a period of several minutes to several hours. In introduction of alkoxycarbonyl at the 7α position, the compound (VII) is allowed to react with an alkali metal cyanide such as potassium cyanide, sodium cyanide, or the like in an alcohol such as methanol, ethanol, or the like and subsequent hydrolysis of cyano intermediate with alcohol such as methanol, ethanol, or the like in the presence of an acid or alkali catalyst; alternatively, the 7-cyano compound provided from the reaction of the compound (VII) with dialkylaluminium cyanide in an aprotic solvent such as benzene, toluene, tetrahydrofuran, or the like is allowed to react with heating in water or an alcoholic solvent such as methanol, ethanol, or the like with an acid or alkali catalyst. The introduction of lower alkyl at the 7α-position is achieved with Grignard reagents, preferably, n-propyl magnesium bromide in an ether solvent such as tetrahydrofuran, ether, or the like.

Eleventh step

In the eleventh step, a halogen or hydroxy group is introduced at the 6 position; the compound (VI) is converted into the enol ether, enol acetate, or enamine derivatives according to conventional techniques, and the product is allowed to react with a halogenating agent such as perchlorylfluoride, N-chlorosuccinimide, N-bromoacetamide, N-bromosuccinimide, or the like to give the halogen derivatives, or by oxidation with an oxidizing agent such as alkaline hydrogen peroxide and subsequent reduction to give the hydroxy derivatives.

Although all of the compounds (VI)–(XI) provided in the manner as mentioned above have a lactone ring, they can be converted into the corresponding salts (e.g. sodium or potassium salt) of hydroxy acid on reaction with 1 equimolar amount of an alkali metal hydroxide dissolved in an aqueous alcoholic solvent such as methanol, ethanol, isopropanol, or the like, under which condition the lactone ring is cleaved as described below.

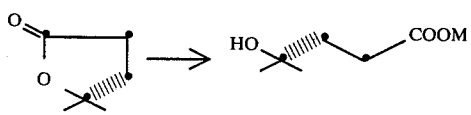

[wherein M is an alkali metal]. The reaction is conducted at room temperature or with heating, and terminates within a perood of several hours.

Alternative to the above mentioned route, the reaction from the compound (II) into the compound (VI) can also be achieved by the other known preparation method [Synthesis, 1980, p. 289–291],

Effects and Uses

The compounds of the present invention have a potent aldosterone-antagonistic activity.

The aldosterone-antagonistic and agonistic activities of the compounds of the present invention were compared with those of spironolactone; the experimental method and results are shown below.

Experimental Method

Bilateral adrenal glands of male SLC-Wister rats (body weight: 180–200 g) are extirpated, and the rats fed with usual foods and 0.45% sodium chloride aqueous solution on the first day; on the second day, lumps of sugar are given in place of usual foods and 0.45% sodium chloride aqueous solution is injected intraperitoneally at a dose of 6 ml per 100 g body weight to the animal 18 hours before the start of collection of the urine; on the third day, 0.45% sodium chloride aqueous solution is injected intraperitoneally at a dose of 6 ml per 100 g body weight, and then the test compound or spironolactone is subcutaneously administered alone or together with aldosterone as a suspension in sesame oil as vehicle; aldosterone is also subcutaneously administered alone to another group of the rats. Two hours after the completion of the administration, collection of the urine is started and the volume of the urine collected over 4 hours is measured. The sodium and potassium contents are determined by atomic absorption spectrometry, from which the sodium to potassium (Na/K) ratio is calculated.

The test compound

A: 17-Hydroxy-3-oxo-17α-pregna-4,6,11-triene-21-carboxylic acid γ-lactone
B: 17-Hydroxy-6α,7α-methylene-3-oxo-17α-pregna-4,11-diene-21-carboxylic acid γ-lactone
C: Potassium 17-hydroxy-6α,7α-methylene-3-oxo-17α-pregna-4,11-diene-21-carboxylate
D: 17-Hydroxy-3-oxo-17α-pregna-1,4,6,11-tetraene-21-carboxylic acid γ-lactone

Result

The result relating to the aldosterone-antagonistic activity is shown in Tables 1–4, and the result relating to the agonistic activity in Tables 5–7.

TABLE 1

| Compounds | Dose (μg/kg) | Number of rats employed | Urine Volume (ml/100 g b.w.) | Na/K ratio |
|---|---|---|---|---|
| Control | — | 8 | 3.43 ± 0.21 | 6.74 ± 0.46 |
| Aldosterone | 1 | 8 | 2.73 ± 0.13 | 2.18 ± 0.30 |
| Aldosterone Spirono-lactone | 1 2,500 | 8 | 3.03 ± 0.15 | 4.44 ± 0.62 |
| Aldosterone A | 1 25,000 | 8 | 3.34 ± 0.21 | 7.01 ± 0.53 |
| Aldosterone A | 1 2,500 | 8 | 2.92 ± 0.26 | 6.23 ± 0.48 |

TABLE 2

| Compounds | Dose (μg/kg) | Number of rats employed | Urine Volume (ml/100 g b.w.) | Na/K ratio |
|---|---|---|---|---|
| Control | — | 8 | 2.43 ± 0.22 | 7.08 ± 0.53 |
| Aldosterone | 1 | 8 | 2.42 ± 0.19 | 2.96 ± 0.35 |
| Aldosterone Spirono-lactone | 1 2,500 | 8 | 2.61 ± 0.09 | 5.89 ± 0.61 |
| Aldosterone B | 1 25,000 | 8 | 2.54 ± 0.14 | 7.19 ± 0.85 |
| Aldosterone B | 1 2,500 | 8 | 3.02 ± 0.27 | 5.62 ± 0.67 |

TABLE 3

| Compounds | Dose (μg/kg) | Number of rats employed | Urine Volume (ml/100 g b.w.) | Na/K ratio |
|---|---|---|---|---|
| Control | — | 8 | 3.71 ± 0.17 | 6.93 ± 0.76 |
| Aldosterone | 1 | 8 | 3.01 ± 0.30 | 3.07 ± 0.23 |
| Aldosterone Spirono-lactone | 1 2,500 | 8 | 2.88 ± 0.26 | 6.03 ± 0.76 |
| Aldosterone C | 1 25,000 | 8 | 3.25 ± 0.18 | 7.70 ± 0.74 |
| Aldosterone C | 1 2,500 | 8 | 2.92 ± 0.25 | 6.77 ± 0.89 |

TABLE 4

| Compounds | Dose (μg/kg) | Number of rats employed | Urine Volume (ml/100 g b.w.) | Na/K ratio |
|---|---|---|---|---|
| Control | — | 7 | 4.32 ± 0.34 | 8.45 ± 0.40 |
| Aldosterone | 1 | 7 | 3.42 ± 0.27 | 3.33 ± 0.34 |
| Aldosterone D | 1 2,500 | 7 | 3.80 ± 0.25 | 6.26 ± 0.49 |
| Aldosterone D | 1 12,500 | 7 | 3.92 ± 0.16 | 7.88 ± 0.41 |

TABLE 5

| Compounds | Dose (μg/kg) | Number of rats employed | Urine Volume (ml/100 g b.w.) | Na/K ratio |
|---|---|---|---|---|
| Control | — | 8 | 2.68 ± 0.21 | 5.50 ± 0.80 |
| Aldosterone | 1 | 8 | 2.68 ± 0.30 | 2.03 ± 0.20 |
| Spironolactone | 25,000 | 7 | 2.68 ± 0.21 | 4.10 ± 0.31 |
| Spironolactone | 2,500 | 7 | 2.87 ± 0.23 | 4.54 ± 0.66 |
| Spironolactone | 250 | 7 | 2.98 ± 0.35 | 3.95 ± 0.39 |

TABLE 6

| Compounds | Dose (μg/kg) | Number of rats employed | Urine Volume (ml/100 g b.w.) | Na/K ratio |
|---|---|---|---|---|
| Control | — | 7 | 3.12 ± 0.11 | 6.63 ± 0.50 |
| Aldosterone | 1 | 7 | 2.63 ± 0.12 | 2.94 ± 0.45 |
| A | 25,000 | 7 | 3.22 ± 0.19 | 5.80 ± 0.29 |
| A | 2,500 | 7 | 2.89 ± 0.17 | 6.45 ± 0.52 |
| B | 25,000 | 7 | 2.58 ± 0.14 | 6.65 ± 0.74 |
| B | 2,500 | 7 | 2.47 ± 0.25 | 6.51 ± 0.71 |

TABLE 7

| Compounds | Dose (μg/kg) | Number of rats employed | Urine Volume (ml/100 g b.w.) | Na/K ratio |
|---|---|---|---|---|
| Control | — | 7 | 2.66 ± 0.29 | 6.73 ± 0.61 |
| Aldosterone | 1 | 7 | 2.31 ± 0.23 | 1.91 ± 0.15 |
| D | 25,000 | 7 | 3.11 ± 0.22 | 7.21 ± 0.85 |
| D | 2,500 | 7 | 2.38 ± 0.17 | 5.44 ± 0.76 |

As shown in Tables 1-4, it is obvious that the compounds of the present invention have a higher aldosterone-antagonistic activity than spironolactone does. Further, the agonistic activity of the test compounds is lower than that of spironolactone as shown in Tables 5-7.

As seen from the fact described above, the compounds of the present invention having a potent aldosterone-antaganostic activity with lower agonistic activity can effectively be used as antihypertensive diuretics.

The compounds of the present ivnention can orally or parenterally be administered, and can be formulated into various dosage forms according to the route of administration. For example, they may be formulated into tablets, capsules, pills, granules, fine granules, aqueous solution, emulsion, and the like. In the formulation, carriers or diluents, such as lactose, sucrose, starch, cellulose, talc, magnesium stearate, magnesium oxide, calcium sulfate, powdered gum arabic, gelatin, sodium alginate, sodium benzoate, stearic acid, and the like may be used. In preparing injections, distilled water for injection, physiological saline, Ringer solution, and the like may be used.

The compounds of the present invention may be administered orally at a dose or doses of about 10 to 200 mg a day for an adult, and intravenously at a dose or doses of about 0.5 to 50 mg.

The compounds provided by the process of this invention are exemplified below.

17-Hydroxy-3-oxo-17α-pregna-4,11-diene-21-carboxylic acid γ-lactone,

Potassium 17-hydroxy-3-oxo-17α-pregna-4,11-diene-21-carboxylate,

17-Hydroxy-3-oxo-17α-pregna-4,6,11-triene-21-carboxylic acid γ-lactone,

Potassium 17-hydroxy-3-oxo-17α-pregna-4,6,11-triene-21-carboxylate,

7α-Acetylthio-17-hydroxy-3-oxo-17α-pregna-4,11-diene-21-carboxylic acid γ-lactone, 17-Hydroxy-3-oxo-7α-trimethylacetylthio-17α-pregna-4,11-diene-21-carboxylic acid γ-lactone, 7α-Benzoylthio-17-hydroxy-3-oxo-17α-pregna-4,11-diene-21-carboxylic acid γ-lactone, 17-Hydroxy-6α,7α-methylene-3-oxo-17α-pregna-4,11-diene-21-carboxylic acid γ-lactone, Potassium 17-hydroxy-6α,7α-methylene-3-oxo-17α-pregna-4,11-diene-21-carboxylate, 17-Hydroxy-3-oxo-17α-pregna-1,4,6,11-tetraene-21-carboxylic acid γ-lactone, Potassium 17-hydroxy-3-oxo-17α-pregna-1,4,6,11-tetraene-21-carboxylate, 17-Hydroxy-3-oxo-17α-pregna-1,4,11-triene-21-carboxylic acid γ-lactone, 17-Hydroxy-6α,7α-methylene-3-oxo-17α-pregna-1,4,11-triene-21-carboxylic acid γ-lactone, 6β-Chloro-17-hydroxy-3-oxo-17α-pregna-4,11-diene-21-carboxylic acid γ-lactone, and the like.

The present invention will be explained in more detail by the following Examples.

EXAMPLE 1

17-Hydroxy-3-oxo-17α-pregna-4,11-diene-21-carboxylic acid γ-lactone 6

1-(a)

4,11-Androstadiene-3,17-dione 2

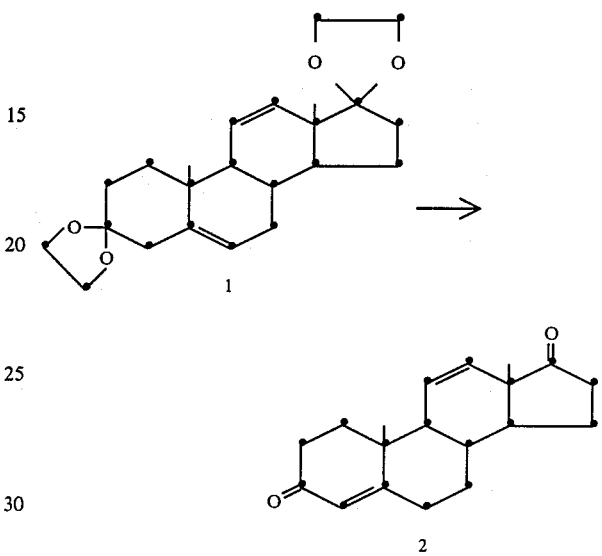

To a solution of 3,17-bis(ethylenedioxy)-5,11-androstadiene 1 (25.28 g, 67.9 mmol) dissolved in a mixture of dioxane (300 ml) and water (100 ml) is added 12 ml of 6N perchloric acid aqueous solution, and the resulting mixture is allowed to react at room temperature for 22 hours. The product is extracted with ethyl acetate. The ethyl acetate layer is washed with a saturated aqueous solution of sodium bicarbonate and water, dried over anhydrous magnesium sulfate, and evaporated. The resulting crystalline product is recrystallized from dichloromethane-ether to give 18.72 g (yield: 97%) of the titled compound 2.

m.p. 171°-174° C.

NMR: $\delta^{CDCl_3}$ 1.00 (s, 3H), 1.17 (s, 3H), 5.50 (d, J=10 Hz, 1H), 5.72 (s, 1H), 5.72 (d.d, J=10 and 2 Hz, 1H).

1-(b)

3-Ethoxy-3,5,11-androstatrien-17-one 3

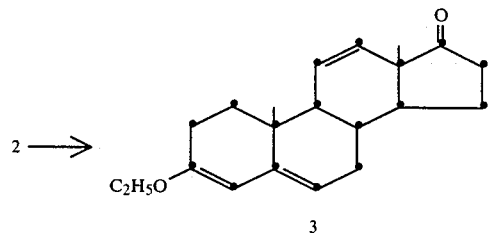

A solution of 37.25 g (131 mmol) of the compound 2 provided in the above step 1-(a), 53 ml (319 mmol) of ethyl orthoformate, and 3 g of p-toluenesulfonic acid dissolved in 450 ml of dioxane is allowed to react at room temperature for 1.5 hours. To the reaction mixture is added 10 ml of pyridine, and the product is extracted with ethyl acetate. The ethyl acetate layer is washed once with a saturated aqueous solution of sodium bicarbonate, and twice with a saturated aqueous solution of sodium chloride, and dried over anhydrous magnesium sulfate, and evaporated. The residue is purified by silica-gel chromatography and eluted with a mixture of benzene-ethyl acetate (9:1), and the eluate is recrystallized from dichloromethane-ether to give 27.68 g (yield: 67.6%) of the titled compound 3.

m.p. 120°–123.5° C.

NMR: $\delta^{CDCl_3}$ 0.95 (s, 3H), 1.00 (s, 3H), 1.30 (t, J=7 Hz, 3H), 2.60 (d, J=5.5 Hz, 1H), 2.82 (d, J=5.5 Hz, 1H), 3.75 (q, J=7 Hz, 2H), 5.13 (s, 1H), 5.13–5.35 (m, 1H), 5.52 (s, 2H).

1-(d)

17-Hydroxy-3-oxo-17α-pregna-4,11-diene-21-carboxylic acid γ-lactone 6

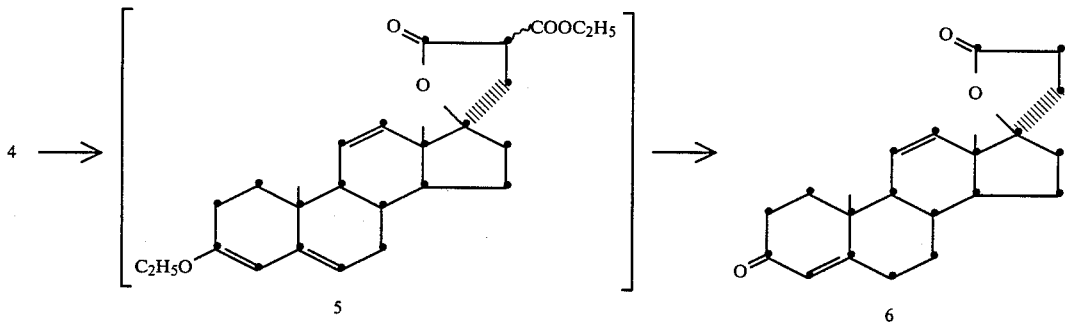

m.p. 153°–156° C.

NMR: $\delta^{CDCl_3}$ 0.97 (s, 3H), 1.31 (t, J=7 Hz, 3H), 3.75 (q, J=7 Hz, 2H), 5.12 (s, 1H), 5.12–5.35 (m, 1H), 5.57 (d, J=10 Hz, 1H), 6.07 (d.d, J=10 and 2 Hz, 1H).

1-(c)

3-Ethoxy-17,20-epoxy-17α-methyl-3,5,11-androstatriene 4

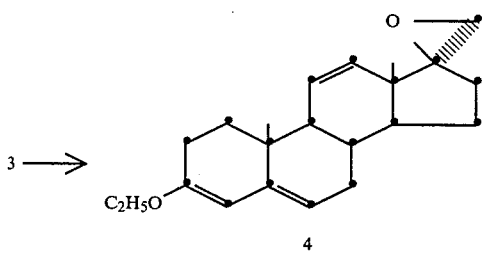

A mixture of 14.15 g (35.4 mmol) of 60% oily sodium hydride and 190 ml of dimethylsulfoxide is allowed to react at 65°–70° C. for about 1 hour until hydrogen gas generation terminates. The reaction mixture is cooled, diluted with 190 ml of tetrahydrofuran, and further cooled to −5°–0° C. To the mixture is dropwise added a solution of 75.8 g (35.4 mmol) of trimethylsulfonium iodide in 350 ml of dimethylsulfoxide with stirring, and then a solution of 27.68 g (88.6 mmol) of the compound 3 provided in the above step 1-(b) in 200 ml of tetrahydrofuran is dropwise added, during which operation the reaction temperature is kept at −5°–0° C. The reaction mixture is then allowed to react at 0° C. for 2 hours, and at room temperature for 15 hours. The product is extracted with ethyl acetate. The ethyl acetate layer is washed 3 times with a saturated aqueous solution of sodium chloride, dried over anhydrous magnesium sulfate, and evaporated. The resulting crystalline residue is recrystallized from dichloromethane-ether-n-pentane to give 8.6 g of the titled compound 4. The mother liquor is purified by chromatography on a column of silica-gel with a mixture of benzene-ethyl acetate (9:1) as eluent to give additional 12.8 g of the titled compound 4. The total amount is 21.4 g (yield: 74.0%).

To an ethanol solution of sodium ethoxide provided from 2.26 g (98.4 mmol) of sodium and 150 ml of ethanol is dropwise added 32.37 g (200 mmol) of diethyl malonate at room temperature, and the mixture is allowed to react for about 10 minutes. The reaction mixture to which is added 21.4 g (65.6 mmol) of the compound 4 provided in the above step 1-(c) is then heated under reflux with stirring for 5 hours. The mixture is cooled to room temperature, evaporated in vacuum to give the residue to which is added a mixture of water-ethanol (9:1) containing 36 g of sodium hydroxide and stirred vigorously at room temperature for 15 hours. The reaction mixture is acidified with conc-hydrochloric acid, and the product is extracted with dichloromethane. The dichloromethane extract is washed with water, dried over anhydrous magnesium sulfate, and evaporated. The resulting crude acidic product is dissolved in 300 ml of xylene, the mixture is placed in a flask equiped with a Dean-Stark water separator containing Molecular sieves 4A and heated under reflux for about 3 hours. Xylene is removed by distillation in vacuum, and the product is purified by chromatography on a column of silica-gel and eluted with a mixture of benzene-ethyl acetate (4:1). The main product is recrystallized from dichloromethane-ether to give 15.96 g (yield: 71.5%) of the titled compound 6.

m.p. 187°–189° C.

NMR: $\delta^{CDCl_3}$ 1.03 (s, 3H), 1.14 (s, 3H), 5.60 (d, J=10 Hz, 1H), 5.77 (s, 1H), 5.93 (d.d, J=10 and 2 Hz, 1H).

IR: $\nu_{max}^{CHCl_3}$ 1615, 1668, 1765 cm$^{-1}$

EXAMPLE 2

Potassium 17-hydroxy-3-oxo-17α-pregna-4,11-diene-21-carboxylate 7

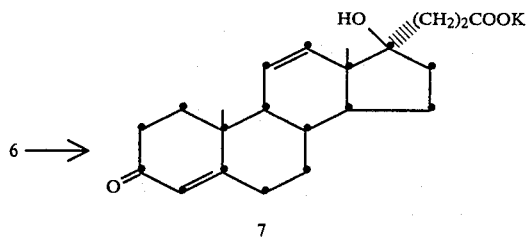

The compound 6 (68 mg, 0.2 mmol) provided in Example 1 is dissolved in 2 ml (0.2 mmol) of 0.1N potassium hydroxide aqueous solution and 3 ml of methanol, the mixture is heated under reflux for 3 hours. The reaction mixture is cooled and evaporated to dryness in vacuum. The resulting crystalline product is recrystallized from methanol-ether to give 750 mg (yield: 99%) of the titled compound 7. m.p. higher than 200° C. (decomp.)

EXAMPLE 3

17-Hydroxy-3-oxo-17α-pregna-4,6,11-triene-21-carboxylic acid γ-lactone 9

3-(a)

3-Ethoxy-17-hydroxy-17α-pregna-3,5,11-triene-21-carboxylic acid γ-lactone 8

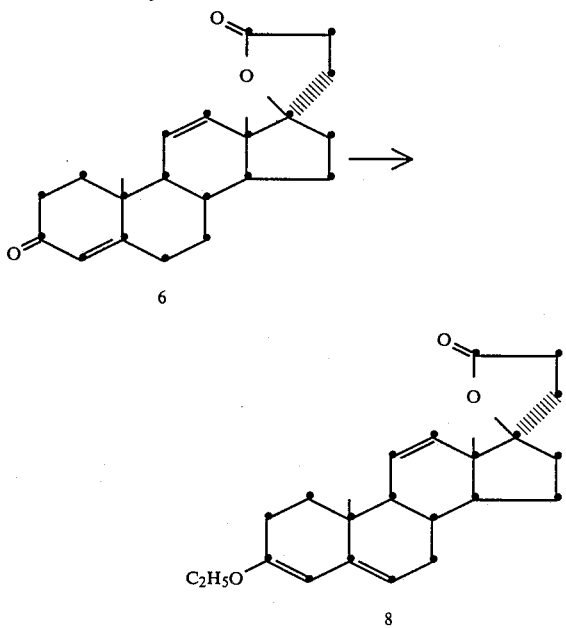

To a solution of 1.70 g (5 mmol) of the compound 6 provided in Example 1 and 2.22 g (15 mmol) of ethyl orthoformate in 10 ml of dioxane is added 15 mg of p-toluenesulfonic acid, and the mixture is allowed to react at room temperature for 1.5 hours. The reaction mixture, to which is added about 0.5 ml of pyridine, is poured into ice-water, and the product is extracted with ethyl acetate. The ethyl acetate layer is washed 3 times with a saturated aqueous solution of sodium chloride, dried over anhydrous magnesium sulfate, and evaporated. The resulting crude product is purified by chromatography on a column of silica-gel and eluted with a mixture of benzene-ethyl acetate (9:1). The main product is recrystallized from dichloromethane-ether to give 1.50 g (yield: 81.2%) of the titled compound 8.

m.p. 138°–139° C.

NMR: $\delta^{CDCl_3}$ 0.93 (s, 3H), 1.03 (s, 3H), 1.28 (t, J=7 Hz, 3H), 3.75 (q, J=7 Hz, 2H), 5.13 (s, 1H), 5.22 (m, 1H), 5.62 (d, J=10 Hz, 1H), 5.87 (d.d, J=10 and 1 Hz, 1H).

3-(b)

17-Hydroxy-3-oxo-17α-pregna-4,6,11-triene-21-carboxylic acid γ-lactone 9

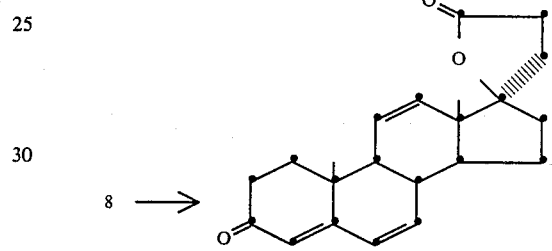

To the compound 8 (1.50 g, 4.06 mmol) provided in the above step 3-(a) dissolved in 15 ml of a mixture of acetone-water (9:1) containing several drops of pyridine is added 1.02 g (4.06 mmol) of 2,3-dichloro-5,6-dicyano-1,4-benzoquinone (purity: 90%), and the mixture is allowed to react at room temperature for 30 minutes. The reaction mixture is evaporated in vacuum, and the product is extracted with dichloromethane. Material insoluble in dichloromethane is removed by passing through a layer of Hyflo Super Cel (John Manville Sales Corp.), and the filtrate is evaporated. The resulting crude product is purified by chromatography on a column of silica-gel and eluted with a mixture of benzene-ethyl acetate (1:2), the resulting main product is crystallized from dichloromethane-ether to give 919 mg (yield: 66.9%) of the titled compound 9.

m.p. 184°–186° C.

NMR: $\delta^{CDCl_3}$ 1.08 (s, 6H), 5.68 (d, J=10 Hz, 1H), 5.70 (s, 1H), 5.87 (d.d, J=10 and 3 Hz), 6.20 (AB type q, J=10 Hz, 2H).

IR: $\nu_{max}^{CHCl_3}$ 1580, 1615, 1660, 1765 cm$^{-1}$

Alternative process
17-Hydroxy-3-oxo-17α-pregna-4,6,11-triene-21-carboxylic acid γ-lactone 9

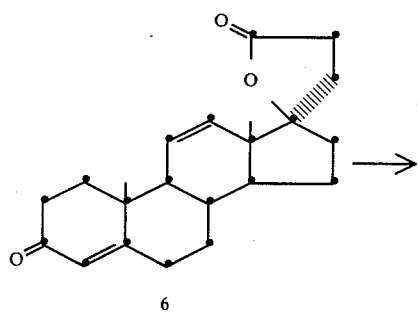
6

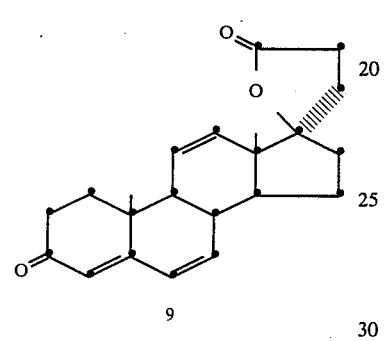
9

The compound 6 (2.5 g, 8.9 mmol) provided in Example 1 and 2.3 g (9.4 mmol) of chloranil are dissolved in a mixture of acetic acid (45 ml) and benzene (18 ml), and the mixture is heated under reflux for 2 hours. The reaction mixture is cooled, and then poured into a mixture of ice-water and dichloromethane containing 29 g of sodium hydroxide. The product is extracted with dichloromethane. The dichloromethane layer is washed with ice-water containing 9 g of sodium hydroxide to liberate insoluble material, which is removed by passing through a layer of Hyflo Super Cel (John Manville Sales Corp.). The dichloromethane layer is separated, washed 3 times with water, dried over anhydrous magnesium sulfate, and evaporated. The residue is purified by chromatography on a column of silica-gel and eluted with a mixture of benzene-ethyl acetate (2:1). The main product is recrystallized from dichloromethane-ether to give 1.21 g (yield: 49%) of the titled compound 9.

EXAMPLE 4

Potassium 17-hydroxy-3-oxo-17α-pregna-4,6,11-triene-21-carboxylate 10

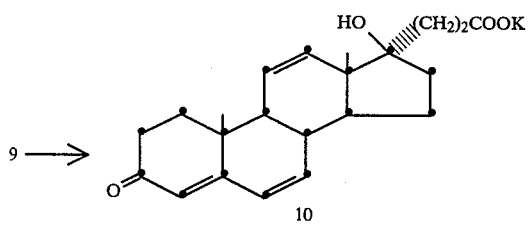

The compound 9 (338 mg, 1 mmol) provided in Example 3 is dissolved in 5 ml of isopropanol and 1 ml of 1N potassium hydroxide aqueous solution, and the mixture is heated under reflux in nitrogen gas for 1.5 hours. The mixture is cooled, and evaporated to dryness in vacuum, and the residue is recrystallized from methanol-ether to give 369 mg (yield: 93.5%) of the titled compound 10.

m.p. 210°–215° C. (decomp.)

EXAMPLE 5

7α-Acetylthio-17-hydroxy-3-oxo-17α-pregna-4,11-diene-21-carboxylic acid γ-lactone 11

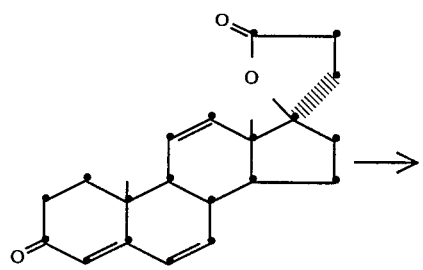
9

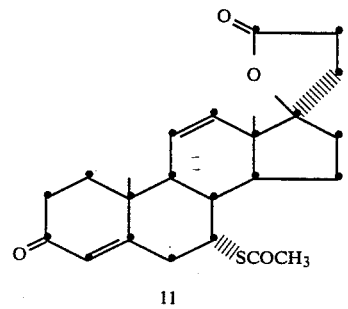
11

The compound 9 (338 mg, 1 mmol) provided in Example 3 is dissolved in 2 ml of thiolacetic acid, and the mixture is heated under reflux for 1.5 hours. The excess amount of thiolacetic acid is distilled off in vacuum, the resulting crude product is purified by chromatography on a column of silica-gel and eluted with a mixture of benzene-ethyl acetate (4:1). The main product is recrystallized from dichloromethane-methanol to give 403 mg (yield: 97.5%) of the titled compound 11.

m.p. 137°–139° C.

NMR: $\delta^{CDCl_3}$ 1.06 (s, 3H), 1.17 (s, 3H), 2.40 (s, 3H), 4.03 (broad.m, 1H), 5.56 (d, J=10 Hz, 1H), 5.70 (s, 1H), 5.88 (d.d, J=10 and 2 Hz, 1H).

IR: $\nu_{max}^{CHCl_3}$ 1620, 1675, 1690, 1765 cm$^{-1}$

EXAMPLE 6

17-Hydroxy-3-oxo-7α-trimethylacetylthio-17α-pregna-4,11-diene-21-carboxylic acid γ-lactone 12

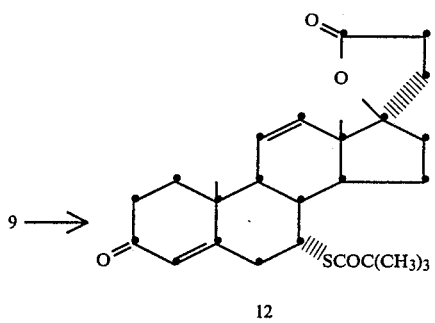

12

The compound 9 (169 mg, 0.5 mmol) provided in Example 3 is dissolved in 0.75 ml of thiopivalic acid, and the mixture is heated under reflux for 75 minutes. The excess amount of thiopivalic acid is distilled off in vacuum, and the residue is purified by chromatography on a column of silica-gel and eluted with a mixture of benzene-ethyl acetate (4:1). The main product is recrystallized from dichloromethaneether to give 223 mg (yield: 97.7%) of the titled compound 12.

m.p. 185°–186° C.

NMR: $\delta^{CDCl_3}$ 1.07 (s, 3H), 1.18 (s, 3H), 1.24 (s, 9H), 4.00 (broad.m, 1H), 5.58 (d, J=10 Hz, 1H), 5.75 (s, 1H), 5.93 (d.d, J=10 and 2 Hz, 1H).

IR: $\nu_{max}^{CHCl_3}$ 1620, 1685, 1765 cm$^{-1}$

EXAMPLE 7

7α-Benzoylthio-17-hydroxy-3-oxo-17α-pregna-4,11-diene-21-carboxylic acid γ-lactone 13

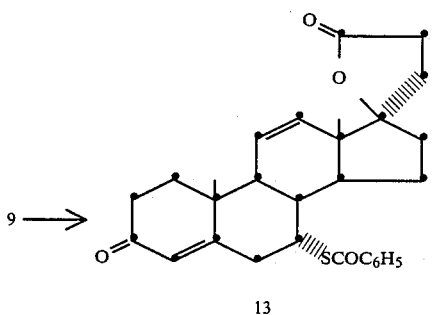

13

A solution of compound 9 (100 mg, 0.3 mmol) provided in Example 3 dissolved in 0.44 ml of thiobenzoic acid is allowed to react at 120° for 45 minutes. The reaction mixture is cooled, poured into ice-water, and the product is extracted with dichloromethane. The dichloromethane layer is washed once with a saturated aqueous solution of sodium carbonate, and twice with a saturated aqueous solution of sodium chloride, dried over anhydrous magnesium sulfate, and evaporated. The residue is purified by silica-gel chromatography and eluted with a mixture of benzene-ethyl acetate (4:1) to give 119 mg (yield: 84%) of the titled compound 13 as noncrystal powder.

NMR: $\delta^{CDCl_3}$ 1.05 (s, 3H), 1.15 (s, 3H), 4.2–4.4 (m, 1H), 5.60 (d.d, J=2 and 10 Hz), 5.94 (d.d, J=3 and 10 Hz), 7.2–7.7 (m, 3H), 7.99 (d.d, J=3 and 9 Hz)

IR: $\nu_{max}^{CHCl_3}$ 1660, 1761 cm$^{-1}$

EXAMPLE 8

17-Hydroxy-6α,7α-methylene-3-oxo-17α-pregna-4,11-diene-21-carboxylic acid γ-lactone 14

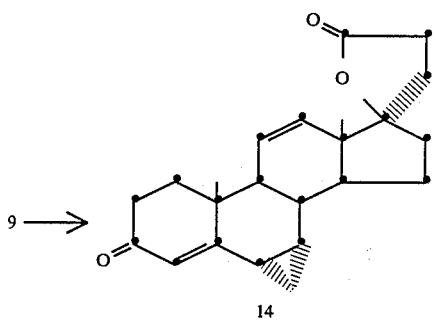

14

To a mixture of 1 g (25 mmol) of 60% oily sodium hydride and 5.5 g (25 mmol) of trimethylsulfoxonium iodide is dropwise added 25 ml of dimethylsulfoxide under cooling with ice-water with stirring. The resulting mixture is stirred at 0° C. for 10 minutes and then at room temperature for 1 hour. The mixture is cooled again at 0° C., and a solution of 1.69 g of the compound 9 provided in Example 3 in dimethylsulfoxide is added thereto. The reaction mixture is allowed to react at 0° C. for 30 minutes and then at room temperature for 17 hours, and poured into ice-water containing 2N hydrochloric acid aqueous solution. The product is extracted with ethyl acetate, the ethyl acetate layer is washed twice with a saturated aqueous solution of sodium chloride, dried over anhydrous magnesium sulfate, and evaporated. The residue is separated by chromatography on a column of silica-gel and eluted with a mixture of benzene-ethyl acetate (4:1). The nonpolar fraction gives 423 mg of a structurally unidentified compound, and the subsequent polar fraction gives 620 mg (yield: 67.5%) of the titled compound 14 as noncrystal powder.

NMR: $\delta^{CDCl_3}$ 1.06 (s, 3H), 1.09 (s, 3H), 5.63 (d, J=11 Hz, 1H), 5.85 (d.d, J=11 and 2 Hz, 1H), 5.93 (s, 1H).

IR: $\nu_{max}^{CHCl_3}$ 1602, 1652, 1765 cm$^{-1}$

EXAMPLE 9

Potassium 17-hydroxy-6α,7α-methylene-3-oxo-17α-pregna-4,11-diene-21-carboxylate 15

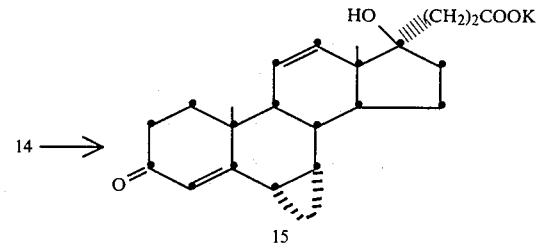

15

A solution of the compound 14 (273 mg, 0.77 mol) provided in Example 8 dissolved in 3 ml of isopropanol and 0.77 ml of 1N potassium hydroxide aqueous solution is heated under reflux for 1.5 hours. The reaction mixture is cooled, evaporated, and the residue is recrystallized from methanol-acetone to give 252 mg (yield: 79.6%) of the titled compound 15.

m.p. 222°–227° C. (decomp.).

EXAMPLE 10

17-Hydroxy-3-oxo-17α-pregna-1,4,6,11-tetraene-21-carboxylic acid γ-lactone 16

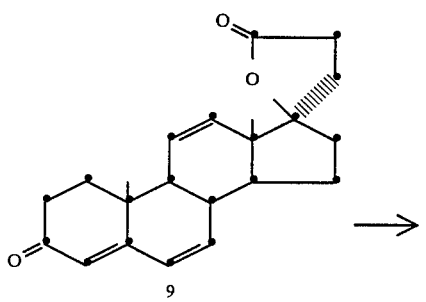

A solution of 300 mg (0.88 mmol) of the compound 9 provided in Example 3 and 277 mg (1.1 mmol) of 2,3-dichloro-5,6-dicyano-1,4-benzoquinone (purity: 90%) dissolved in 3 ml of dioxane is heated under reflux with stirring for 1 hour. The mixture is cooled, the insoluble material is removed by filtration, and the product is isolated from the filtrate with dichlofomethane. The dichloromethane layer is washed once with 5% sodium hydroxide aqueous solution, and twice with a saturated aqueous solution of sodium chloride, dried over anhydrous magnesium sulfate, and evaporated. The residue is purified by chromatography on a column of silica-gel and eluted with a mixture of benzene-ethyl acetate (2:1). The main product is recrystallized from dichloromethane-ether to give 233 mg (yield: 79%) of the titled compound 16.

m.p. 85°–88° C.

NMR. $\delta^{CDCL_3}$ 1.12 (s, 3H), 1.20 (s, 3H), 5.93 (s, 2H), 6.05 (s, 1H), 6.11 (d.d, J=2 and 8.5 Hz, 1H), 6.29 (d.d, J=2 and 9 Hz, 1H), 6.32 (d.d, J=2 and 8.5 Hz), 7.17 (d, J=9 Hz, 1H).

IR: $\nu_{max}^{CHCl_3}$ 1600, 1654, 1764 cm$^{-1}$

EXAMPLE 11

Potassium 17-hydroxy-3-oxo-17α-pregna-1,4,6,11-tetraene-21-carboxylate 17

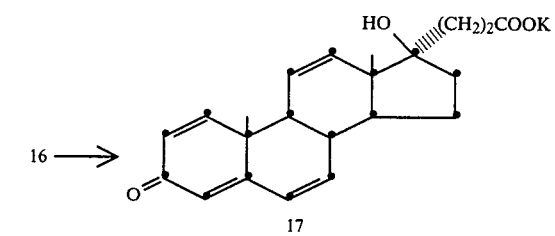

To a solution of 336.4 mg (1 mmol) of the compound 16 provided in Example 10 dissolved in 5 ml of isopropanol is added 1 ml of 1N potassium hydroxide aqueous solution. The mixture is stirred under reflux for 2 hours and evaporated, and the residue is dissolved in methanol, treated with active carbon and filtered. The filtrate is evaporated to give 363 mg (yield: 91%) of the titled compound 17 as amorphous powder.

IR: $\nu_{max}^{Nujol}$ 1568 (broad), 1610 (sh), 1660, 1680, 2500–3600 cm$^{-1}$

EXAMPLE 12

17-Hydroxy-3-oxo-17α-pregna-1,4,11-triene-21-carboxylic acid γ-lactone 18

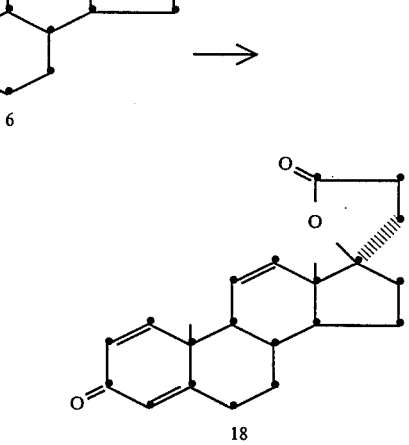

To a solution of 500 mg (1.47 mmol) of the compound 6 provided in Example 1 dissolved in 30 ml of t-butanol are added 85 μl of pyridine and 326 mg (2.94 mmol) of selenium dioxide purified by sublimation, and the mixture is heated under reflux for 20 hours, and then cooled. The insoluble material is removed by filtration with Hyflo Super Cel (Johns Manville Sales Corp.), and the filtrate is extracted with ethyl acetate. The ethyl acetate layer is washed once with a saturated aqueous solution of sodium chloride, dried over anhydrous magnesium sulfate, treated with active carbon, and evaporated. The residue is purified by silica-gel chromatography and eluted with a mixture of benzene-ethyl acetate (4:1). The main product is recrystallized from dichloromethane-ether to give 282 mg (yield: 57%) of the titled compound 18.

m.p. 97°–100° C.

NMR: $\delta^{CDCl_3}$ 1.09 (s, 3H), 1.22 (s, 3H), 5.76 (d, J=10.5 Hz, 1H), 5.96 (d.d, J=10.5 and 2 Hz, 1H), 6.13 (s, 1H), 6.28 (d.d, J=10.5 and 2 Hz, 1H), 7.15 (d, J=10.5 Hz, 1H).

IR: $\nu^{CHCl_3}_{max}$ 1600, 1618, 1659, 1762 cm$^{-1}$

Alternative process

A solution of 100 mg (0.29 mmol) of the above compound 6 and 70 mg (0.28 mmol) of 2,3-dichloro-5,6-dicyano-1,4-benzoquinone (purity: 90%) dissolved in 1 ml of benzene is heated under reflux with stirring for 6 hours. The mixture is cooled, and the insoluble material is removed by filtration, and the product is isolated from the filtrate with dichloromethane. The dichloromethane layer is washed once with 5% sodium hydroxide aqueous solution, and twice with a saturated aqueous solution of sodium chloride, dried over anhydrous magnesium sulfate, and evaporated. The residue is purified by silica-gel chromatography and eluted with a mixture of benzene-ethyl acetate (2:1). The main product is recrystallized from dichloromethane-ether to give 56 mg (yield: 57%) of the titled compound 18.

EXAMPLE 13

17-Hydroxy-6α,7α-methylene-3-oxo-17α-pregna-1,4,11-triene-21-carboxylic acid γ-lactone 19

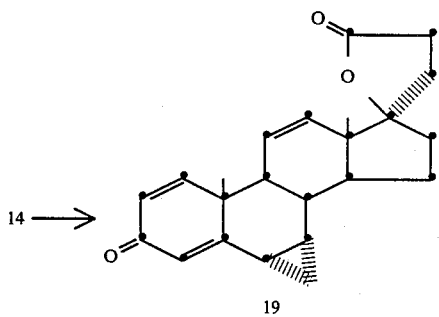

A solution of 40 mg (0.11 mmol) of the compound 14 provided in Example 8 and 31 mg (0.12 mmol) of 2,3-dichloro-5,6-dicyano-1,4-benzoquinone (purity: 90%) dissolved in 1.5 ml of dioxane is heated under reflux with stirring for 2 hours. The mixture is cooled and evaporated in vacuum, and the product is extracted with dichloromethane. Material insoluble in dichloromethane is removed by passing through Hyflo Super Cel (Johns Manville Sales Corp.), and the filtrate is evaporated. The resulting crude product is purified by chromatography on a column of silica-gel and eluted with a mixture of benzene-ethyl acetate (2:1) to give 19 mg (yield: 47.8%) of the titled compound 19 as noncrystal powder.

NMR: $\delta^{CDCl_3}$ 1.10 (s, 3H), 1.24 (s, 3H), 5.79 (d, J=12 Hz, 1H), 5.90 (d.d, J=12 and 3 Hz, 1H), 6.21 (d.d, J=12 and 1 Hz, 1H), 6.30 (s, 1H), 7.07 (d, J=12 Hz, 1H).

IR: $\nu^{CHCl_3}_{max}$ 1600, 1620, 1660, 1667 cm$^{-1}$

EXAMPLE 14

6β-Chloro-17-hydroxy-3-oxo-17α-pregna-4,11-diene-21-carboxylic acid γ-lactone 20

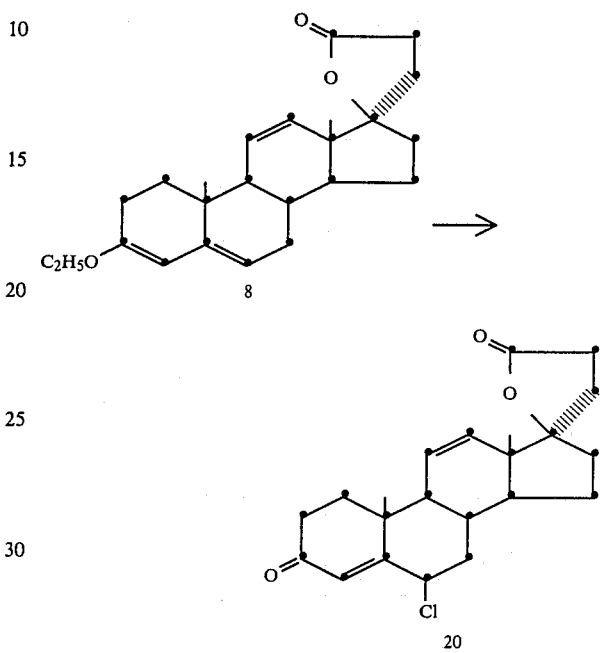

To a solution of 184 mg (0.5 mmol) of the compound 8 provided in Example 3-(a) and 73 mg (0.55 mmol) of N-chlorosuccinimide dissolved in 5 ml of acetone and 0.5 ml of water is added 3 drops of pyridine, and the mixture is allowed to react at room temperature for 2 hours. The reaction mixture is poured into ethyl acetate, and the product is extracted with ethyl acetate. The ethyl acetate layer is washed 3 times with a saturated aqueous solution of sodium chloride, dried over anhydrous magnesium sulfate, and evaporated. The residue is purified by silica-gel chromatography and eluted with a mixture of benzene-ethyl acetate (2:1). The main product is recrystallized from dichloromethane-ether to give 120 mg (yield: 64%) of the titled compound 20.

m.p. 194°–196° C.

NMR: $\delta^{CDCl_3}$ 1.20 (s, 3H), 1.42 (s, 3H), 4.83 (s, 1H), 5.61 (d, J=10 Hz, 1H), 5.93 (s, 1H), 5.96 (d.d, J=3 and 10 Hz, 1H).

IR: $\nu^{CHCl_3}_{max}$ 1610, 1678, 1762 cm$^{-1}$.

What we claim is:
1. The compounds:
   a. 17-hydroxy-3-oxo-17α-pregna-1,4,6,11-tetraene-21-carboxylic acid γ-lactone;
   b. potassium 17-hydroxy-3-oxo-17α-pregna-1,4,6,11-tetraene-21-carboxylate;
   c. 17-hydroxy-3-oxo-17α-pregna-4,6,11-triene-21-carboxylic acid γ-lactone;
   d. potassium 17-hydroxy-3-oxo-17α-pregna-4,6,11-triene-21-carboxylate;
   e. 17-hydroxy-6α,7α-methylene-3-oxo-17α-pregna-4,11-diene-21-carboxylic acid γ-lactone;

f. potassium 17-hydroxy-6α,7α-methylene-3-oxo-17α-pregna-4,11-diene-21-carboxylate;
g. 17-hydroxy-6α,7α-methylene-3-oxo-17α-pregna-1,4,11-triene-21-carboxylic acid γ-lactone;
h. 17-hydroxy-3-oxo-7α-trimethylacetylthio-17α-pregna-4,11-diene-21-carboxylic acid γ-lactone;
i. 17-hydroxy-3-oxo-17α-pregna-4,11-diene-21-carboxylic acid γ-lactone;
j. potassium 17-hydroxy-3-oxo-17α-pregna-4,11-diene-21-carboxylate;
k. 7α-acetylthio-17-hydroxy-3-oxo-17α-pregna-4,11-diene-21-carboxylic acid γ-lactone;
l. 7α-benzoylthio-17-hydroxy-3-oxo-17α-pregna-4,11-diene-21-carboxylic acid γ-lactone;
m. 17-hydroxy-3-oxo-17α-pregna-1,4,11-triene-21-carboxylic acid γ-lactone, and
n. 6β-chloro-17-hydroxy-3-oxo-17α-pregna-4,11-diene-21-carboxylic acid γ-lactone.

2. The compound claimed in claim 1, namely, 17-hydroxy-3-oxo-17α-pregna-1,4,6,11-tetraene-21-carboxylic acid γ-lactone.

3. The compound claimed in claim 1, namely, potassium 17-hydroxy-3-oxo-17α-pregna-1,4,6,11-tetraene-21-carboxylate.

4. The compound claimed in claim 1, namely, 17-hydroxy-3-oxo-17α-pregna-4,6,11-triene-21-carboxylic acid γ-lactone.

5. The compound claimed in claim 1, namely, potassium 17-hydroxy-3-oxo-17α-pregna-4,6,11-triene-21-carboxylate.

6. The compound claimed in claim 1, namely, 17-hydroxy-6α,7α-methylene-3-oxo-17α-pregna-4,11-diene-21-carboxylic acid γ-lactone.

7. The compound claimed in claim 1, namely, potassium 17-hydroxy-6α,7α-methylene-3-oxo-17α-pregna-4,11-diene-21-carboxylate.

8. The compound claimed in claim 1, namely, 17-hydroxy-6α,7α-methylene-3-oxo-17α-pregna-1,4,11-triene-21-carboxylic acid γ-lactone.

9. The compound claimed in claim 1, namely, 17-hydroxy-3-oxo-7α-trimethylacetylthio-17α-pregna-4,11-diene-21-carboxylic acid γ-lactone.

10. The compound according to claim 1, namely 17-hydroxy-3-oxo-17α-pregna-4,11-diene-21-carboxylic acid γ-lactone.

11. The compound according to claim 1, namely potassium 17-hydroxy-3-oxo-17α-pregna-4,11-diene-21-carboxylate.

12. The compound according to claim 1, namely 7α-acetylthio-17-hydroxy-3-oxo-17α-pregna-4,11-diene-21-carboxylic acid γ-lactone.

13. The compound according to claim 1, namely 7α-benzoylthio-17-hydroxy-3-oxo-17α-pregna-4,11-diene-21-carboxylic acid γ-lactone.

14. The compound according to claim 1, namely 17-hydroxy-3-oxo-17α-pregna-1,4,11-triene-21-carboxylic acid γ-lactone.

15. The compound according to claim 1, namely 6β-chloro-17-hydroxy-3-oxo-17α-pregna-4,11-diene-21-carboxylic acid γ-lactone.

* * * * *